United States Patent [19]
Joo et al.

[11] Patent Number: 5,418,146
[45] Date of Patent: May 23, 1995

[54] PROCESS FOR PREPARING DIPEPTIDES

[75] Inventors: Dae K. Joo; Kwang H. Kim; Il Hyun; Min S. Han; Bun S. Lim, all of Seoul, Rep. of Korea

[73] Assignee: Miwon Co., Ltd., Seoul, Rep. of Korea

[21] Appl. No.: 993,466

[22] Filed: Dec. 15, 1992

Related U.S. Application Data

[63] Continuation of Ser. No. 666,063, Mar. 7, 1991, abandoned.

[30] Foreign Application Priority Data

Nov. 24, 1990 [KR] Rep. of Korea .................. 90-19109

[51] Int. Cl.⁶ ............................................. C12P 21/00
[52] U.S. Cl. .................................. 435/68.1; 435/711; 435/712; 435/212; 435/219; 435/220; 435/839
[58] Field of Search ............... 435/68.1, 71.2, 71.1, 435/220, 839, 212, 219

[56] References Cited

U.S. PATENT DOCUMENTS

| | | | |
|---|---|---|---|
| 4,086,136 | 4/1978 | Isowa et al. | 435/68.1 |
| 4,116,768 | 9/1978 | Isowa et al. | 435/68.1 |
| 4,165,311 | 8/1979 | Isowa et al. | 260/112.5 |
| 4,212,946 | 7/1980 | Nonaka et al. | 435/68.1 |
| 4,256,836 | 3/1981 | Isowa et al. | 435/68.1 |
| 4,284,721 | 8/1981 | Oyama et al. | 435/68.1 |
| 4,339,534 | 7/1982 | Johansen | 435/68.1 |
| 4,521,514 | 6/1985 | Oyama et al. | 435/68.1 |
| 4,935,355 | 6/1990 | Ulmer et al. | 435/68.1 |
| 5,002,872 | 3/1991 | Gross | 435/68.1 |

OTHER PUBLICATIONS

J. Org. Chem., 46, 5241–5242 (1981).
Biochem. 17(24), 5220 (1978).

*Primary Examiner*—Shailendra Kumar
*Attorney, Agent, or Firm*—Birch, Stewart, Kolasch & Birch

[57] ABSTRACT

This invention relates to an improvement in a method for manufacturing dipeptides by coupling N-blocked aspartic acid and a phenylalanine lower alkyl ester in a medium containing a water-miscible organic solvent mixture in the presence of an immobilized metalloprotease so that a continuous reaction is established with stable enzyme activity.

6 Claims, No Drawings

PROCESS FOR PREPARING DIPEPTIDES

This application is a continuation, of application Ser. No. 07/666,063 filed on Mar. 7, 1991, now abandoned.

BACKGROUND OF THE INVENTION

1. Field of the Invention

The invention relates to a process for preparing dipeptides and more particularly, to a process for the preparation of dipeptides represented by the following formula (I) which comprises reacting N-blocked aspartic acid represented by the following formula (II) with a lower alkyl ester of phenylalanine represented by the following formula (III) in the presence of an organic solvent mixture and immobilized enzyme,

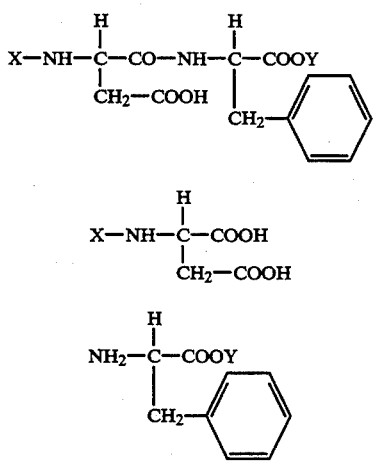

wherein X is a protective group used in peptide synthesis and Y is a lower alkyl group.

2. Description of the Prior Art

Generally, it is well known that protease can be used for forming peptide bonds in the reverse reaction of protein decomposition. A number of conventional methods have been proposed for favoring the reverse reaction toward synthesis of dipeptides. U.S. Pat. No. 4,165,311 to Isowa et al discloses a process for producing an addition compound which includes reacting a dipeptide and amino acid ester in an aqueous medium in the presence of a protease. However, only a soluble enzyme may be used. Generally, such a soluble enzyme is not only expensive but is unstable in soluble form so that it can only be utilized in very limited industrial applications. In order to overcome such limitations, research has been conducted for several years. As a result, it is possible to improve the enzyme stability by immobilizing techniques. However, in such an addition compound forming system, it is practically impossible to use any kind of immobilized enzymes due to the difficulties of enzyme separation therefrom. U.S. Pat. No. 4,284,721 to Oyama et al. discloses that a water-containing immobilized metallo-proteinase in an organic solvent immiscible with water is used to favor the peptide bond formation. J. Org. Chem., 46, p. 5241 (1981) published by Oyama et al discloses that, due to an immediate transfer of the product toward the water-immiscible organic solvent, the reaction rate as well as the equilibrium yield are relatively good although they are lower than those in the aqueous medium.

Furthermore, although the Oyama et al reference employs an immobilized enzyme which is stable in the organic solvent, since the enzyme requires a certain water content, the water-immiscible organic solvent inevitably requires to contain two phases. However, such a two phase medium limits the continuous operation of synthetic processes, particularly, a process of the packed bed column reactor and stirred tank reactor. In the stirred tank reactor, an attrition of the enzyme necessarily occurs. Furthermore, even though the enzyme is in an immobilized form, it is not satisfactorily stable.

To avoid these disadvantages of the water-immiscible solvent medium, the use of an organic solvent miscible with water has been considered. However, in such a medium, a micro-environmental change between the water disposed around the immobilized enzymes and the organic solvent causes feedback inhibition so that the reaction rate inevitably decreases.

On the other hand, however, the fact that an organic cosolvent can shift the reversible peptide forming reaction toward synthesis has been reported by Homandberg et al (Biochem. 17 (24), 5220 (1978)).

SUMMARY OF THE INVENTION

Accordingly, it is an object of the present invention to provide an improved process for preparing dipeptides to overcome the above drawbacks.

Another object of the present invention is to provide a method for manufacturing dipeptides of the following formula (I) which comprises reacting N-substituted aspartic acid of the following formula (II) with a phenylalanine lower alkyl ester of the following formula (III) in an organic solvent mixture miscible with water in the presence of immobilized metallo-protease,

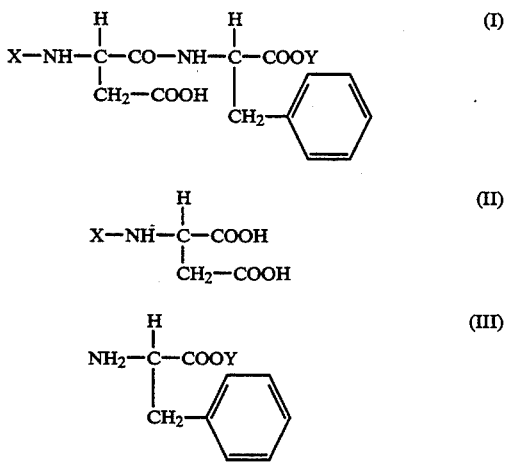

wherein X is a protective group which is generally used in a peptide synthesis and Y is a lower alkyl group of X. Preferred examples are urethane type groups such as benzyloxy-carbonyl, p-methoxybenzyloxycarbonyl, t-butoxycarbonyl, benzoyl, and the like. Preferred examples of Y are $C_1$-$C_4$ alkyl groups, preferably methyl or ethyl groups. The blocked aspartic acids of formula (II) and phenylalanine lower alkyl esters of formula (III) are prepared by generally known methods.

A further object of the present invention is to provide a process for the preparation of dipeptides which comprises providing a water-miscible solvent medium which provides for advantageously easier product recovery and substrate preparation by causing improved solubility properties.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to an improvement in a method for manufacturing dipeptides by coupling N-blocked aspartic acid and a phenylalanine lower alkyl ester in a medium containing a water-miscible organic solvent mixture in the presence of an immobilized metallo-protease so that a continuous reaction is established with very stable enzyme activity.

DESCRIPTION OF THE PREFERRED EMBODIMENTS

The enzymes employed in this invention are proteases, preferably metallo-proteases from the Bacillus species such as *subtilis, stearothermophilus*, and the like.

In the present invention, the enzymes are used in an immobilized form. The methods are based on general techniques including physical adsorption, covalent bonding, inclusion, and cross linking methods.

The reaction is carried out in an aqueous medium which contains up to about 70% of an organic solvent or a combination of several solvents. Preferred organic solvents are alkanols, e.g. methanol and ethanol, glycols, e.g. ethylene glycol and polyethylene glycols of molecular weight 200 to 2000, dimethyl formamide, dimethyl sulfoxide, acetonitrile, and tetrahydrofuran. Further, it is necessary that the aqueous medium containing the organic solvent or a combination of the organic solvents has an ability to dissolve both of the starting materials of the formulas (II) and (III) of the reaction and the product of the formula (I). The selected aqueous medium preferably allows for a reaction rate and equilibrium yield as high as possible. The enzyme stability must also be maintained in the same medium.

It is preferable to employ high concentrations of each of the starting materials according to the present invention, because the higher concentrations will allow for a faster reaction rate. The concentrations of each of the starting materials are such that the starting materials and the product remain soluble in the medium, preferably at concentration ranges from about 0.25 to 1.0M.

The quantity of the N-substituted aspartic acid and phenylalanine lower alkyl ester employed according to the present invention is generally in the molar ratio range of from about 1:1 to 1:5, since it is favorable to have a higher molar concentration of the phenylalanine ester than the N-substituted aspartic acid.

The present invention includes no particular restriction with regard to the quantity of the immobilized enzyme used in the reaction since this only affects the reaction time.

The pH of the reaction mixture is maintained in a range which provides the maximum enzyme activity in the selected reaction medium. Generally, this is in a range of from about 5 to 8, preferably from about 5.5 to 7.0. The pH can be adjusted by adding NaOH prior to the reaction.

The reaction temperature is usually in the range of from about 5° to 50° C., preferably from about 30° to 50° C.

The reaction time depends on the reaction temperature, the concentration of the starting materials, and the quantity of the immobilized enzyme. Generally, a reaction time of from about 0.5 to 10 hours suffices.

The process of the present invention is carried out in a column packed with the immobilized enzyme by introducing the starting materials in the aqueous solvent mixture. The process permits the reaction to be continuously carried out and thus is particularly advantageous for an industrial application. The process can also be carried out in a conventional reactor with stirring although the stirred reactor may possibly cause attrition of the immobilized enzyme.

The produced dipeptide ester product is ordinarily recovered as a solid from the reaction mixture. The product is obtained in a high purity without additional steps of purification. Unreacted amino acid components, unrecovered dipeptide product and the immobilized enzyme can be recovered, recycled and reused. Particularly, the enzyme in the column can be used repeatedly for a long time.

The blocking group of the N-substituted aspartic acid can be readily removed from the dipeptide ester by known methods of hydrogenation such as catalysis in the presence of palladium.

The present invention is particularly useful for the aspartame production process when a methyl group is employed as the lower alkyl group of the phenylalanine lower alkyl ester. Aspartame is useful as a sweetening material in food stuffs and has the chemical name alpha-L-aspartyl-L-phenylalanine methyl ester.

The following examples are included merely to aid in the understanding of the invention and variations may be made without departing from the scope of the invention.

EXAMPLE 1

XAD-7 resin (Rohm & Haas) was washed and equilibrated with Tris buffer (20 mM, pH 7.0 containing 10 mMCaCl$_2$). 12.5 g of Thermoase (Daiwa Kasei, 10,000 [PU], wherein one unit is defined as that liberating material which has absorbance at 280 nm in the casein digest equivalent to 1 micromole of tyrosine in 1 minute at 35° C.) was added to the resin of 100 ml and agitated for 5 hours. After loading, the beads were fixed with 10% solution of glutaraldehyde and washed with buffer.

1.19 g (5.0 mmol) of N-benzoyl-L-aspartic acid and 1.79 g (10.0 mmol) of L-phenylalanine methyl ester were added to a flask which contained 50 ml of 50% acetonitrile in water containing 5 mM CaCl$_2$. The pH of the solution was adjusted to 6.0 with 10M NaOH. The solution was admixed with 4 g of suction filtered immobilized enzyme prepared above. Thereafter, the reaction were carried out with stirring for 4 hours at 40° C. After completion of the reaction, the immobilized enzyme was separated by filtration. The pH of the filtrate was then adjusted to 3.7 by 10 molar hydrochloric acid. Resulting slurry was filtered and washed with water to give N-benzoyl-L-aspartyl-L-phenylalanine methyl ester.

The crystal thus obtained was subjected to a high performance liquid chromatography analysis to find that the yield of the product was 82.4% in the reaction.

The conditions used for the HPLC analysis were as shown below:

Column: Econosphere (Alltech) C18, 250×4.6 mm, 5 micron

Eluent: 0.1M of phosphate buffer containing 25% of acetonitrile and 12% of methanol, pH 3.5
Flow rate: 1.0 ml/mn
Detector: UV 254 nm

EXAMPLE 1

The procedure of Example 1 was followed excepting that the quantity of N-benzoyl-L-aspartic acid was 2.38 g (10.0 mmol) and in place of acetonitrile, dimethyl sulfoxide was used. N-benzoyl-L-aspartyl-L-phenylalanine methyl ester was obtained in the yield of 52.1%.

EXAMPLE 2

The procedure of Example 2 was followed excepting that the pH was adjusted to 6.5 and the reaction time was 8 hours at 30° C. N-benzoyl-L-aspartyl-L-phenylalanine methyl ester was obtained in the yield of 46.7%.

EXAMPLE 4

The procedure of Example 1 was followed excepting that 1.34 g (5.0 mmol) of N-benzyloxycarbonyl-L-aspartic acid was used and the reaction time was 3 hours. N-benzyloxycarbonyl-L-aspartyl-L-phenylalanine methyl ester was obtained in the yield of 83.5%.

EXAMPLE 5

The procedure of Example 1 was followed excepting that the quantity of Thermoase was 5 g and the reaction time was 13 hours. N-benzoyl-L-aspartyl-L-phenylalanine methyl ester was obtained in the yield of 78.9%.

EXAMPLE 6

The procedure of Example 1 was followed excepting that in place of acetonitrile, 50% dimethyl formamide was used and the reaction time was 6 hours. N-benzoyl-L-aspartyl-L-phenylalanine methyl ester was obtained in the yield of 65 7%.

EXAMPLE 7

The procedure of Example 1 was followed excepting that: in place of acetonitrile, 40% of dimethyl formamide and 15% of ethylene glycol was used, pH was adjusted to 5.8, and the reaction time was 6 hours. N-benzoyl-L-aspartyl-L-phenylalanine methyl ester was obtained in the yield of 57.6%.

EXAMPLE 8

The procedure of Example 4 was followed excepting that: in place of acetonitrile, 45% of dimethyl sulfoxide and 15% of polyethylene glycol 400 was used, the reaction time was 5 hours, the pH was 6.2. N-benzylexycarbonyl-L-aspartyl-L-phenylalanine methyl ester was obtained in the yield of 85 1%.

EXAMPLE 9

The procedure of Example 1 was followed excepting that: In place of acetonitrile, 30% of acetonitrile and 25% of polyethylene glycol 600 was used, the reaction time was 6 hours, the pH was adjusted to 6.5. N-benzoyl-L-aspartyl-L-phenylalanine methyl ester was obtained in the yield of 78.5%.

EXAMPLE 10

The procedure of Example 9 was followed excepting that: the quantity of N-benzoyl-L-aspartic acid was 2.85 g (10 mmol) and of the L-phenylalanine methyl ester was 2.69 g (15 mmol), in place of polyethylene glycol 600, polyethylene glycol 200 was used, the reaction time was 7 hours. N-benzoyl-L-aspartyl-L-phenylalanine methyl ester was obtained in the yield of 64.2%.

EXAMPLE 11

The procedure of example 10 was followed excepting that: in place of acetonitrile, dimethyl formamide was used, the reaction time was 5 hours, the pH was adjusted to 6.2 N-benzoyl-L-aspartyl-L-phenylalanine methyl ester was obtained in the yield of 52.4%.

EXAMPLE 12

The procedure of Example 11 was followed excepting that; in place of stirring, a column packed with immobilized enzyme prepared as in the Example 1 was used, the feed material was made in the same concentration as in the Example 11. The feed was allowed to enter into the column continuously in a flow rate of 0.9 $H^{-1}$. The concentration of N-benzoyl-L-aspartyl-L-phenylalanine methyl ester in the product solution was 115 mM. The unreacted starting materials was separated from the product by the same technique of the Example 1 and was recycled to the next run. The bioreactor operation was continued for a month.

EXAMPLE 13

The procedure of Example 12 was followed excepting that: instead of dimethyl formamide, 40% of dimethyl sulfoxide was used, the flow rate was 12 $H^{-1}$, the concentration of N-benzoyl-L-aspartic acid and L-phenylalanine methyl ester was 100 mM and 200 mM, respectively.

The concentration of N-benzoyl-L-aspartyl-L-phenylalanine methyl ester in the product solution was 75mM. The bioreactor run was continued for 2 months.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing dipeptides of an N-substituted-L-aspartyl-L-phenylalanine lower alkyl ester of the following formula (I), which comprises reacting N-substituted-L-aspartic acid of the following formula (II) with a phenylalanine lower alkyl ester of the following formula (III) in a medium comprising water; an organic solvent selected from the group consisting of methyl alcohol, ethyl alcohol, acetonitrile, dimethyl formamide, dimethyl sulfoxide and tetrahydrofuran; and polyethylene glycol of molecular weight from 200 to 2000; in the presence an immobilized metalloprotease, wherein said metalloprotease enzyme is thermolysin from *Bacillus subtilis* or thermolysin from *Bacillus stearothermophilus*,

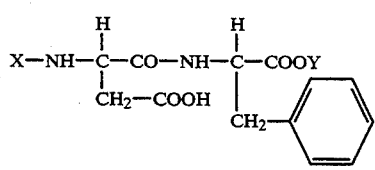

-continued

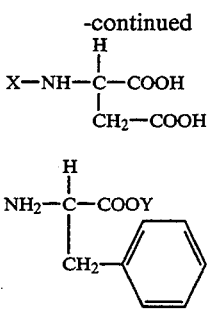

wherein X is a protective group and Y is a lower alkyl group.

2. The process of claim 1, wherein X is selected from the group consisting of benzoyl, benzyloxycarbonyl, p-methoxybenzyloxycarbonyl, and t-butoxycarbonyl, and Y is selected from the group consisting of methyl, ethyl, propyl and butyl.

3. The process of claim 1, wherein polyethylene glycol is present at 15 to 25 percent.

4. The process of claim 3, wherein polyethylene glycol is present at 25 percent and said organic solvent is present at 40 percent.

5. The process of claim 4, wherein said organic solvent is dimethyl sulfoxide.

6. The process of claim 5, wherein X is selected from the group consisting of benzoyl, benzyloxycarbonyl, p-methoxybenzyloxycarbonyl, and t-butoxycarbonyl, and Y is selected from the group consisting of methyl, ethyl, propyl and butyl.

* * * * *